(12) United States Patent
Chiou et al.

(10) Patent No.: US 9,943,477 B2
(45) Date of Patent: Apr. 17, 2018

(54) EMULSION COMPOSITIONS CONTAINING A NOVEL PRESERVATIVE SYSTEM

(71) Applicant: L'OREAL, Paris (FR)

(72) Inventors: Catherine Chiou, Saddle Brook, NJ (US); Joyce Beauchamp, Roselle Park, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/136,714

(22) Filed: Dec. 20, 2013

(65) Prior Publication Data

US 2015/0174054 A1    Jun. 25, 2015

(51) Int. Cl.
| | | |
|---|---|---|
| A61K 47/30 | (2006.01) | |
| A61K 8/92 | (2006.01) | |
| A61K 8/34 | (2006.01) | |
| A61K 8/368 | (2006.01) | |
| A61K 8/891 | (2006.01) | |
| A61K 8/892 | (2006.01) | |
| A61K 8/893 | (2006.01) | |
| A61Q 19/00 | (2006.01) | |

(52) U.S. Cl.
CPC .............. *A61K 8/922* (2013.01); *A61K 8/34* (2013.01); *A61K 8/345* (2013.01); *A61K 8/368* (2013.01); *A61K 8/891* (2013.01); *A61K 8/892* (2013.01); *A61K 8/893* (2013.01); *A61Q 19/00* (2013.01); *A61K 2800/10* (2013.01); *A61K 2800/30* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 4,268,499 A | 5/1981 | Keil | |
| 4,917,882 A | 4/1990 | Strobridge | |
| 5,601,811 A | 2/1997 | Gallagher et al. | |
| 6,447,793 B2* | 9/2002 | Aust ...................... | A01N 39/00 252/380 |
| 6,524,598 B2 | 2/2003 | Sunkiel et al. | |
| 6,696,049 B2 | 2/2004 | Vatter et al. | |
| 7,262,217 B2 | 8/2007 | Baranger et al. | |
| 8,216,555 B2 | 7/2012 | Nieuwenhuijsen | |
| 8,299,127 B2 | 10/2012 | Anjing et al. | |
| 8,461,206 B2 | 6/2013 | Dalko | |
| 8,481,594 B2 | 7/2013 | Boulle et al. | |
| 8,603,502 B2 | 12/2013 | Boulle et al. | |
| 8,609,117 B2 | 12/2013 | Boulle et al. | |
| 2003/0064046 A1 | 4/2003 | Omura et al. | |
| 2003/0118524 A1* | 6/2003 | Karpov .................. | A61K 8/345 424/59 |
| 2007/0128137 A1 | 6/2007 | Yoshimi et al. | |
| 2007/0264210 A1 | 11/2007 | Robinson | |
| 2007/0274932 A1* | 11/2007 | Suginaka et al. ............... | 424/59 |
| 2009/0035236 A1 | 2/2009 | Maes et al. | |
| 2010/0136068 A1* | 6/2010 | Perier ...................... | A61K 8/11 424/401 |
| 2010/0179222 A1 | 7/2010 | Boulle et al. | |
| 2010/0183692 A1* | 7/2010 | Natsch ......................... | 424/405 |
| 2010/0310617 A1 | 12/2010 | Zhang et al. | |
| 2011/0256077 A1 | 10/2011 | Hayakawa | |
| 2012/0088836 A1 | 4/2012 | Dalko | |
| 2012/0322876 A1 | 12/2012 | Kermorvan et al. | |
| 2013/0142740 A1* | 6/2013 | Cziryak .................. | A01N 37/10 424/60 |
| 2013/0345317 A1 | 12/2013 | Chiou | |

FOREIGN PATENT DOCUMENTS

| | | |
|---|---|---|
| CN | 1793822 A | 6/2006 |
| EP | 1027883 A2 | 8/2000 |
| EP | 1671680 A1 | 6/2006 |
| EP | 1990372 A2 | 11/2008 |
| FR | 2847469 A1 | 5/2004 |
| FR | 2847470 A1 | 5/2004 |
| FR | 2909552 A1 | 6/2008 |
| FR | 2921254 A1 | 3/2009 |
| FR | 2921255 A1 | 3/2009 |
| FR | 2940053 A1 | 6/2010 |
| FR | 2951375 A1 | 4/2011 |
| FR | 2953718 A1 | 6/2011 |
| FR | 2954122 A1 | 6/2011 |

(Continued)

OTHER PUBLICATIONS

C. Tran, J.F. Michelet, L. Simonetti, F. Fiat, A. Garrigues, A. Potter, E. Segot, R.E.B. Watson, C.E.M. Griffiths, O. De Lacharriere, In vitro and in vivo studies with tetra-hydro-jasmonic acid (LR2412) reveal its potential to correct signs of skin ageing, Journal of the European Academy of Dermatology and Venereology 2013 European Academy of Dermatology and Venereology, p. 1-9, DOI: 10.1111/jdv.12113.

M. Vonka, J. Kosek, Modelling the morphology evolution of polymer materials undergoing phase separation, Chemical Engineering Journal, 2012, p. 1-11, http://dx.doi.org/10.1016/j.cej.2012.06.091.

U.S. Appl. No. 14/136,471, filed Dec. 20, 2013, Chiou.
U.S. Appl. No. 14/136,562, filed Dec. 20, 2013, Galdi.
U.S. Appl. No. 14/136,634, filed Dec. 20, 2013, Chiou.
U.S. Appl. No. 14/136,714, filed Dec. 20, 2013, Chiou.

(Continued)

*Primary Examiner* — Jared D Barsky

(74) *Attorney, Agent, or Firm* — McNees Wallace & Nurick LLC

(57) ABSTRACT

The present invention is directed to an emulsion composition, comprising: (i) from about 0.01 to about 1% by weight of at least one aromatic alcohol; (ii) from about 0.01 to about 1% by weight of at least one aromatic carboxylic acid; and (iii) from about 0.01 to about 0.5 % by weight of at least one chlorophenyl glyceryl ether; and wherein the composition does not require use of parabens, ethanol and/or glycols in order to preserve the composition.

19 Claims, No Drawings

(56) References Cited

FOREIGN PATENT DOCUMENTS

| | | |
|---|---|---|
| FR | 2964865 A1 | 3/2012 |
| FR | 2973693 A1 | 10/2012 |
| FR | 2977478 A1 | 1/2013 |
| FR | 2988291 A1 | 9/2013 |
| FR | 2988292 A1 | 9/2013 |
| JP | 2001205061 A | 7/2001 |
| WO | 9924028 A1 | 5/1999 |
| WO | 2000069423 A1 | 11/2000 |
| WO | 2010000584 A2 | 1/2010 |
| WO | 2011054600 A1 | 5/2011 |
| WO | 2012084699 A2 | 6/2012 |
| WO | 2012084701 A2 | 6/2012 |
| WO | 2012136564 A2 | 10/2012 |
| WO | 2012136818 A2 | 10/2012 |
| WO | 2012143645 A2 | 10/2012 |
| WO | 2013007637 A2 | 1/2013 |
| WO | 2013007647 A1 | 1/2013 |
| WO | PCT/US2013/045613 | 6/2013 |

OTHER PUBLICATIONS

U.S. Appl. No. 13/529,113, filed Jun. 21, 2012, US-2013-0345317-A1, Chiou.
U.S. Appl. No. 13/529,059, filed Jun. 21, 2012, Chiou.
U.S. Appl. No. 13/855,495, filed Apr. 2, 2013, Chiou.

* cited by examiner

EMULSION COMPOSITIONS CONTAINING A NOVEL PRESERVATIVE SYSTEM

FIELD OF THE INVENTION

The present invention is directed to compositions containing a novel preservative system and methods of using said compositions. More specifically, the present invention is directed to a water-in-oil emulsion composition, comprising: (i) from about 0.01% to about 1% by weight of at least one aromatic alcohol; (ii) from about 0.01% to about 1% by weight of at least one aromatic carboxylic acid; and (iii) from about 0.01% to about 0.5% by weight of at least one chlorophenyl glyceryl ether; and wherein the composition does not require use of parabens, ethanol and/or glycols in order to preserve the composition.

BACKGROUND OF THE INVENTION

It is common practice to introduce chemical preservatives into cosmetic or dermatological compositions, these preservatives being intended to combat the growth of microorganisms in these compositions, which would otherwise make them unsuitable for use. It is in particular necessary to protect compositions against microorganisms capable of growing inside the composition and also against those which the user might introduce therein while handling it, in particular when taking up products in jars with the fingers.

The effectiveness of the preservatives conventionally used is variable and their formulation can pose problems of formulation, such as of incompatibility, or even of destabilization, in particular of emulsions. Furthermore, they may be the cause of undesirable side effects (irritation, allergy) in particular on consumers with sensitive skin. Thus, chemical preservatives commonly used are in particular parabens and formaldehyde-releasing compounds; but these preservatives have, however, the drawback of causing irritation, in particular on sensitive skin, when they are present at relatively high levels. Other known preservatives are organic hydroxy acids; but they may also give rise to irritation due to their desquamating effect on the skin, which is not always well tolerated.

Many conventional preservatives such as, for example, parabens, are constantly being scrutinized due to negative media attention and/or changes in regulatory or safety requirements. In response thereto, formulators have increasingly turned to the use of alcohol (ethanol) as a biocide to protect cosmetic products from microbial spoilage. However, to be an effective biocide, a high concentration of ethanol must be used in the formulas. Unfortunately, high concentrations of ethanol render the manufacture and handling of such products hazardous. Moreover, high levels of said alcohol also result in consumer-perceived drying of skin.

In response to the above-referenced drawback associated with the use of ethanol, formulators have also turned to the use of glycols having mid-sized alkyl chain lengths for their anti-microbial activity. Mid-sized alkyl chain glycols comprise glycols having $C_5$ to $C_{12}$ alkyl chains, such as, for example, pentylene glycol, hexylene glycol, caprylyl glycol, and decylene glycol, and mixtures thereof. However, the surface-active properties of these glycols, most often, also cause the instability of an emulsion, particularly for water-in-oil (W/O) emulsions. These glycols tend to possess surfactant-like properties which in turn have a negative effect on the composition in view of being present in the form of an emulsion, thereby resulting in the emulsion becoming unstable.

Inverse (W/O) emulsions are notoriously difficult to preserve due to the fact that microorganisms can be lodged in the external, continuous oil phase, making it difficult for the preservative ingredients to counteract. Thus an effective preservation system is imperative to provide adequate product protection and ensure consumer's safety.

BRIEF SUMMARY OF THE INVENTION

Disclosed herein is a preservative system for use in topical compositions. It has been found that a preservative system using (i) from about 0.01% to about 1% by weight of at least one aromatic alcohol; (ii) from about 0.01% to about 1% by weight of at least one aromatic carboxylic acid; and (iii) from about 0.01% to about 0.5% by weight of at least one chlorophenyl glyceryl ether yields a composition which does not require use of parabens, ethanol and/or glycols with $C_5$ to $C_{12}$ alkyl chains as preservatives.

The present invention is also directed to a method for preserving an emulsion composition, and especially a water-in-oil emulsion composition, by adding thereto the above-described preservative system.

DETAILED DESCRIPTION OF THE INVENTION

The present invention relates to a unique preservative system that prevents microbial growth and proliferation without the need for the use of parabens, ethanol and/or glycols with $C_5$ to $C_{12}$ alkyl chains as preservatives. Not only are these above-mentioned preservatives avoided, but the present invention's composition also yields a milder preservative system that mitigates adverse effects such as irritation and allergic responses. In addition, the disclosed preservative system is able to effectively inhibit microorganism proliferation in packaging containers considered as being the most difficult to preserve, such as pots and jars, which require consumers to insert their fingers into the container in order to remove product therefrom.

Other than in the operating examples, or where otherwise indicated, all numbers expressing quantities of ingredients and/or reaction conditions or ratios are to be understood as being modified in all instances by the term "about" which encompasses±10%.

A "physiologically acceptable medium" or "cosmetically acceptable medium" means a medium which is not toxic and can be applied to the skin, lips, hair, scalp, lashes, brows, nails or any other cutaneous region of the body. The composition of the invention may especially constitute a cosmetic or dermatological composition.

The term "paraben-free" as used herein means that the composition contains less than 0.2% by weight of parabens.

The term "ethanol-free" as used herein means that the composition contains less than 3% by weight of ethanol.

The term "glycol-free" as used herein means that the composition contains less than 1% by weight of glycols with $C_5$ to $C_{12}$ alkyl chains.

The term "keratinous substrate" as used herein means skin, lips, hair, scalp, lashes, brows, nails or any other cutaneous region of the body.

The subject composition can be provided in a plethora of forms, including but not limited to creams, liquid, gel, cream-gel, lotion, serum, a powder or a solid tube, and may optionally be packaged as an aerosol and may be in the form of a mousse or a spray, prepared according to the usual methods.

Aromatic Alcohol

The preservative composition also contains about 0.01% to about 1% by weight of at least one aromatic alcohol. As used herein, the term "aromatic alcohol" means any compound that is liquid at room temperature and atmospheric pressure, comprising at least one entity chosen from benzene and naphthalene rings and at least one alcohol function (OH) directly linked to the ring or linked to at least one substituent of the ring. In at least one embodiment, the alcohol function may be on a substituent of the benzene or naphthalene ring.

Examples of aromatic alcohols that may be used in the composition include, but are not limited to: benzyl alcohol, benzoylisopropanol, benzyl glycol, phenoxyethanol, dichlorobenzyl alcohol, methylphenylbutanol, phenoxyisopropanol, phenylisohexanol, phenylpropanol, phenylethyl alcohol, and mixtures thereof.

Preferably the aromatic alcohol is phenoxyethanol.

At least one aromatic alcohol is generally present in the composition of the present invention in an amount ranging from about 0.01% to 1% by weight; such as from about 0.1% to 0.8% by weight; such as from about 0.2% to 0.7% by weight, based on the total weight of the composition.

Aromatic Carboxylic Acid

Aromatic carboxylic acids or salts generally include those chosen from benzoic acid, para-anisic acid, anisic acid, caffeic acid, chlorogenic acid, diphenolic acid, ferulic acid, hippuric acid, hydroxycinnamic acid, phenylthioglycolic acid, salicylic acid, acetylsalicylic acid, phthalic acid, salified forms thereof, and combinations thereof.

Preferably the aromatic carboxylic acid used is anisic acid, in the form of alkali or alkaline-earth metal salts, ammonium salts or salts with an organic amine, or one of its $C_{1-4}$ alkyl esters.

The anisic acid used in the present invention may be used as it is or may be present in the form of an alkali or alkaline-earth metal salt, an ammonium salt or a salt with an organic amine, or in the form of a $C_{1-4}$ alkyl ester. The alkyl group of the ester may be linear or branched and there may be mentioned, by way of examples, methyl, ethyl, n-propyl, isopropyl, n-butyl and tert-butyl groups.

By way of examples of anisic acid salt or ester, there may be mentioned in particular sodium anisate, potassium anisate, methyl anisate, ethyl anisate, propyl anisate or butyl anisate.

In at least one embodiment, the at least one aromatic carboxylic acid is p-anisic acid or para-anisic acid.

At least one aromatic carboxylic acid, or salt thereof is generally present in the composition of the present invention in an amount ranging from about 0.01% to 1% by weight; such as from about 0.05% to 0.5% by weight; such as from about 0.1% to 0.3% by weight, based on the total weight of the composition.

Chlorophenyl Glyceryl Ethers

Chlorophenyl glyceryl ethers include, but are not limited to, chlorphenesin, i.e., chlorophenoxy-1,2-propanediol and derivatives thereof.

A particularly preferred aromatic alcohol for use in the present invention is chlorphenesin.

The chlorophenyl glyceryl ether will typically be present in the composition in an amount of from about 0.01% to about 0.5% by weight, preferably from about 0.05% to about 0.4% by weight, and most preferably from about 0.1% to about 0.3% by weight, all weights based on the total weight of the composition.

Further, preferably the combined weight percent of the aromatic carboxylic acid, aromatic alcohol, and chlorophenyl glyceryl ether, together forming the preservative system, is less than 1.7%, based on the total weight of the composition; preferably less than 1.3%; more preferably less than 1%.

Moreover, preferably the combined weight percent of the aromatic carboxylic acid, aromatic alcohol, chlorophenyl glyceryl ether, and any additional preservative or any material known to have anti-microbial activity in the composition is less than about 2.2%.

In another embodiment of the present invention, the composition may further include additional multi-functional ingredients with anti-microbial properties. Well-known examples of such ingredients include, but are not limited to, chelators, such as disodium EDTA; solvents, such as propanediol; and mixtures thereof.

In yet another embodiment of the present invention, the pH value of the water phase can be adjusted to a range of from about pH 4.0 to about pH 6.7, which is deemed optimal for preserving the final product from microbial contamination and spoilage.

Cosmetically Acceptable Aqueous Carrier

The cosmetically acceptable aqueous carrier comprises water. It may, however, if desired, also comprise alcohol, organic solvents, hydrocarbons, esters, silicones, and mixtures thereof.

The compositions according to the invention may be prepared according to techniques that are well known to those skilled in the art, in particular those intended for the preparation of emulsions of oil-in-water, water-in-oil, silicone-in-water, and/or water-in-silicone type. They may be in particular in the form of a simple or complex emulsion (O/W, W/O, O/W/O, W/O/W and/or W/Si emulsions) such as a cream or a milk, in the form of a gel or a cream-gel, oil, or in the form of a lotion, a powder or a solid tube, and may optionally be packaged as an aerosol and may be in the form of a mousse or a spray. These compositions are prepared according to the usual methods.

Particularly, the compositions according to the invention may be in the form of an oil-in-water or water-in-oil emulsion.

The emulsions generally contain at least one emulsifier chosen from amphoteric, anionic, cationic and nonionic emulsifiers, which are used alone or as a mixture. The emulsifiers are appropriately chosen according to the emulsion to be obtained (W/O or O/W).

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name "DC 5225 C" by the company Dow Corning, and alkyldimethicone copolyols such as laurylmethicone copolyol sold under the name "Dow Corning 5200 Formulation Aid" by the company Dow Corning; cetyldimethicone copolyol, such as the product sold under the name Abil EM 90R by the company Evonik, and the mixture of cetyldimethicone copolyol, of polyglyceryl isostearate (4 mol) and of hexyl laurate, sold under the name Abil WE O9 by the company Evonik. One or more co-emulsifiers may also be added thereto, which may be chosen advantageously from the group comprising polyol alkyl esters. Polyol alkyl esters that may especially be mentioned include glycerol and/or sorbitan esters, for example polyglyceryl isostearate, such as the product sold under the name Isolan GI 34 by the company Evonik, sorbitan isostearate, such as the product sold under the name Arlacel 987 by the company Croda, sorbitan glyceryl isostearate, such as the product sold under the name Arlacel 986 by the company Croda, PEG-30 dipolyhydroxy stearate, such as the product sold under the name Arlacel 135 by the company Croda and mixtures thereof.

For the O/W emulsions, examples of emulsifiers that may be mentioned include nonionic emulsifiers such as oxyalkylenated (more particularly polyoxyethylenated) fatty acid esters of glycerol such as the mixture of glyceryl stearate and PEG-100 stearate sold, for example, by the company ICI under the trade name Arlacel 165; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name Montanov 202 by the company SEPPIC. According to one particular embodiment of the invention, the mixture of the alkylpolyglucoside as defined above with the corresponding fatty alcohol may be in the form of a self-emulsifying composition as described, for example, in document WO-A-92/06778.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters (for instance, $C_{12}$-$C_{15}$ alkyl benzoate, octyl palmitate, isopropyl palmitate and triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Among the organic solvents that may be mentioned are lower alcohols and polyols. These polyols may be chosen from glycols and glycol ethers, for instance ethylene glycol, propylene glycol, butylene glycol, dipropylene glycol or diethylene glycol.

In another embodiment of the invention, the subject compositions are formulated as water-in-silicone emulsions in which the continuous oily phase comprises at least one silicone oil. When the compositions of the invention are formulated as water-in-silicone emulsions, the silicone oils are preferably present in a proportion of at least 5 percent and preferably ranging from 10 percent to 45 percent by weight with respect to the total weight of the emulsion. The oil phase of the water-in-oil emulsions according to the invention can additionally comprise one or more hydrocarbon-comprising oil(s) in a proportion preferably ranging up to 40 percent by weight with respect to the total weight of the fatty phase of the emulsion.

Oils that may be used in the W/Si composition may include for example: silicone oils, for instance volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes; mixtures thereof. Particularly representative of such oils are volatile silicone oils, such as cyclomethicones, in order to impart greater fastness towards water of the coloration on the skin, easier and more homogeneous spreading of the composition and shorter drying times.

For the W/Si emulsions, examples of emulsifiers generally include polyether-modified silicones having a long chain of dimethyl siloxane units which carry polyethoxy-polypropoxy units in the chain and at the ends. Examples include PEG/PPG-18/18 dimethicone, PEG-10 Dimethicone, PEG-12 Dimethicone, and PEG/PPG-19/19 Dimethicone sold by Dow Corning under the name Dow Corning® BY 11-030.

According to yet another embodiment of the present invention, the oil phase of the composition may also include an emulsifying cross-linked siloxane elastomer. If present, it will typically be employed at a concentration, by weight, of from about 0.1% to about 20%, or alternatively from about 0.3% to about 10%, or alternatively from about 0.5% to about 7%, based upon the weight of the composition.

Examples of suitable emulsifying crosslinked siloxane elastomers, include, but are not limited to, substituted or unsubstituted dimethicone/copolyol crosspolymer, dimethicone and dimethicone/PEG-10/15 crosspolymers, substituted or unsubstituted dimethicone/polyglyceryl crosspolymer, dimethicone and dimethicone/polyglycerin-3 crosspolymer. Such suitable emulsifying crosslinked siloxane elastomers are sold or made, for example, under the names of "KSG-210" a polyether-modified crosspolymer with an INCI name of "dimethicone (and) dimethicone/PEG-10/15 crosspolymer", and "KSG-710" a polyglycerin-modified crosspolymer with an INCI name of "dimethicone (and) dimethicone/polyglycerin-3 crosspolymer", both available from Shin-Etsu Silicones of America, Inc. (Akron, Ohio).

Optional Ingredients

The composition may comprise at least one auxiliary ingredient, including for example active ingredients, film forming agents, surfactants, conditioning agents, adjuvants, self-tanners, colorants, skin care active agents and mixtures thereof.

Among the active agents that may be mentioned are:
UV filters for sunscreens;
antipollution agents and/or free-radical scavengers;
depigmenting agents and/or propigmenting agents;
antiglycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
desquamating agents;
moisturizers;
anti-inflammatory agents;
agents acting on the energy metabolism of cells;
insect repellants;
Substance P or CGRP antagonists.

The compositions, in an embodiment of the present invention, can employ at least one aesthetic modifier. Aesthetic modifiers can be used to enhance the texture of the composition. For example, the compositions of the current invention can have a matte, powdery, non-greasy, soft texture. Aesthetic modifiers can be chosen from: Nylon-12, polymethylsilsesquioxane, styrene/acrylates copolymer, silica, starches and modified starches, silicone resins and/or mixtures thereof.

The composition may also comprise standard cosmetic adjuvants chosen especially from fatty substances, organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, propellants, acidifying or basifying agents, co-emulsifiers or any other ingredient usually used in cosmetics and/or dermatology.

The pH of the internal, dispersed water phase will generally range from about 4 to about 6.7. In at least one embodiment, the pH may range from about 4.5 to about 6, and may be adjusted to the desired value by means of acidifying or basifying agents that are well known to a person skilled in the art.

The composition of the present invention may also contain at least one tactile modifier. Suitable tactile modifiers include, but are not limited to nylon, silica, and mixtures thereof.

The composition of the present invention may also contain at least one colorant. Preferably, such colored compositions can be cosmetic compositions such as, for example, lip compositions (for example, lipstick or liquid lip colors or lip gloss), body tints, bronzers, self-tanners, mascaras, eye shadow, nail polish or foundations. According to this embodiment, the at least one colorant is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and sub-ranges there between.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

The pigments, which may be used according to the present invention, may be chosen from white, colored, inorganic, organic, polymeric, non-polymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present the pigment is generally present in the composition of the present invention in an amount ranging from about 0% to about 15% by weight; such as from about 0.01% to about 10% by weight; such as from about 0.1% to about 5% by weight, all weights being based on the weight of the composition as a whole.

The composition of the present invention may contain emollients. Suitable emollients include, but are not limited to, mineral oil; petrolatum; $C_7$-$C_{40}$ branched chain hydrocarbons; $C_1$-$C_{30}$ alcohol esters of $C_1$-$C_{30}$ carboxylic acids; $C_1$-$C_{30}$ alcohol esters of $C_2$-$C_{30}$ dicarboxylic acids; monoglycerides of $C_1$-$C_{30}$ carboxylic acids; diglycerides of $C_1$-$C_{30}$ carboxylic acids; triglycerides of $C_1$-$C_{30}$ carboxylic acids; ethylene glycol monoesters of $C_1$-$C_{30}$ carboxylic acids; ethylene glycol diesters Of $C_1$-$C_{30}$ carboxylic acids; propylene glycol monoesters Of $C_1$-$C_{30}$ carboxylic acids; propylene glycol diesters of $C_1$-$C_{30}$ carboxylic acids; $C_1$-$C_{30}$ carboxylic acid monoesters and polyesters of sugars, for example, sefa cottonate (sucrose polycottonseedate); polydialkylsiloxanes; polydiarylsiloxanes; polyalkarylsiloxanes; cyclomethicones having 3 to 9 silicon atoms; vegetable oils; hydrogenated vegetable oils; polypropylene glycol $C_4$-$C_{20}$ alkyl ethers; di $C_8$-$C_{30}$ alkyl ethers; and mixtures thereof.

Needless to say, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The present invention will be better understood from the examples that follow, all of which are intended for illustrative purposes only and are not meant to unduly limit the scope of the invention in any way.

EXAMPLES

The present invention is further described in terms of the following non-limiting examples. Unless otherwise indicated, all parts and percentages are on a weight-by-weight percentage basis.

TABLE 1

Inventive Examples

| Phase | INCI Name | Ex. 1 | Ex. 2 | Ex. 3 |
|---|---|---|---|---|
| A | DIMETHICONE/PEG-10/15 CROSSPOLYMER | 1.25 | 1.25 | 1.25 |
| A | PEG-10 DIMETHICONE | 0.1 | 0.07 | |
| A | DIMETHICONE (and) DIMETHICONOL | 1 | | |
| A | DIMETHICONE | 13.7 | 10.7 | 8.7 |
| A | *SIMMONDSIA CHINENSIS* (JOJOBA) BUTTER | | | 2 |
| B | WATER | QS 100 | QS 100 | QS 100 |
| B | GLYCERIN | 15 | 15 | 30 |
| B | PROPANEDIOL | 5 | 5 | |
| B | DISODIUM EDTA | 0.1 | 0.1 | 0.1 |
| B | SODIUM CITRATE | 0.2 | 0.2 | 0.2 |
| B | SODIUM CHLORIDE | 0.8 | 0.5 | 0.5 |
| B | p-ANISIC ACID | 0.15 | 0.15 | 0.15 |
| B | CHLORPHENESIN | 0.3 | 0.3 | 0.3 |
| B | PHENOXYETHANOL | 0.3 | 0.5 | 0.7 |
| C | POLYMETHYLSILSESQUIOXANE | | 1 | 0.5 |
| C | FRAGRANCE | 0.25 | | |
| | Total (%) | 100 | 100 | 100 |
| | Observation after 8 weeks at 45° C. | Stable | Stable | Stable |

TABLE 2

Comparative Examples

| Phase | INCI Name | Ex. 4 | Ex. 5 | Ex. 6 | Ex. 7 |
|---|---|---|---|---|---|
| A | DIMETHICONE/PEG-10/15 CROSSPOLYMER | 1.25 | 1.25 | 1.25 | 1.25 |
| A | PEG-10 DIMETHICONE | | 0.1 | | 0.1 |
| A | LAURYL PEG-9 POLYDIMETHYL-SILOXYETHYL DIMETHICONE | | | 0.1 | |
| A | DIMETHICONE (and) DIMETHICONOL (88/12) | 2 | 1 | | |
| A | DIMETHICONE | 13.7 | 13.7 | 13.7 | 13.7 |
| B | WATER | QS 100 | QS 100 | QS 100 | QS 100 |
| B | GLYCERIN | 15 | 15 | 15 | 15 |
| B | PROPANEDIOL | 5 | 5 | 5 | 5 |
| B | DISODIUM EDTA | 0.1 | 0.1 | 0.1 | 0.1 |
| B | SODIUM CITRATE | 0.2 | 0.2 | 0.2 | 0.2 |
| B | SODIUM CHLORIDE | 0.8 | 0.8 | 0.8 | 0.8 |
| B | p-ANISIC ACID | 0.15 | | | 0.15 |
| B | PHENOXYETHANOL | | 0.3 | 0.5 | 0.3 |
| B | CAPRYLYL GLYCOL | | | 0.3 | |
| B | ALCOHOL DENAT. | | | | |
| B | NIACINAMIDE | 3 | | | |
| C | VINYL DIMETHICONE/METHICONE SILSESQUIOXANE CROSSPOLYMER | | 0.5 | 0.5 | 0.5 |
| | Total (%) | 100 | 100 | 100 | 100 |
| | Observation after 8 weeks at 45° C. | Stable | Stable | Phase separated | Stable |

In making each of the examples in Tables 1 and 2, the following procedure is used. The ingredients of Phase A (oil phase) were placed in a main beaker and were mixed well with a propeller mixer at about 600-700 RPM and set aside. The ingredients of Phase B (aqueous) were mixed together in a side beaker with a propeller mixer at about 600-700 RPM until all solids were dissolved, giving a clear solution. If needed, Phase B (aqueous) was gently heated to about 40-45° C. until all solids were dissolved. The mixture of aqueous phase ingredients (Phase B) was slowly added to the mixed ingredients of Phase A (oil phase) using a propeller mixer over a period of 10-15 minutes for an about 1 kg batch. As the viscosity of the mixture increased, the stirring speed was increased from 700 rpm to about 1200 rpm. As the aqueous phase is mixed into the oil phase, a water-in-oil emulsion was formed. Optionally, the ingredients of phase C were added to the batch and were mixed into the water-in-oil emulsion.

Microbiological Study Results

Examples 1 to 7 underwent microbiological study per the following protocol:
1. The product was inoculated with saline suspensions made out of 24 hour culture of bacteria and yeast isolates and 5 days culture of mold isolate utilizing the following microorganisms:
   1.1 *Pseudomonas aeruginosa* 19429
   1.2 *Escherichia coli* 8739
   1.3 *Staphylococcus aureus* 6538
   1.4 *Enterococcus faecalis* 33186
   1.5 *Candida albicans* 10231
   1.6 *Aspergillus niger* 6275;
2. Initial concentration of microorganisms in the suspension was approximately 1.0E+8;
3. Inoculation rate was 1%;
4. Final concentration of microorganisms in the product was approximately 1.0E+6;
5. Number of surviving microorganisms was monitored at 7, 14 and 28 days after inoculation by the aerobic plate count method;
6. Logarithmic reduction of microorganisms was calculated from the theoretical initial concentration of microorganism in the product.

Products were evaluated by the initial preservative challenge test. For products meeting the passing criteria, a separate sample was subjected to accelerated aging conditions (8 weeks at 45° C.), and inoculation was repeated according to steps 1 through 6 of the protocol. Therefore, the microbiological studies assessed the initial preservative efficacy (T0M) and the stability of the preservation system after an accelerated aging period (T2M).

Example 1

Inventive Example

| Microorganisms | Inoculum CFU/g | (T2M/45) CFU/g | | |
|---|---|---|---|---|
| | | 7 Days | 14 Days | 28 Days |
| *Escherichia coli* | 2.7E6 | <200 | <200 | <200 |
| *Pseudomonas aeruginosa* | 3.5E6 | <200 | <200 | <200 |
| *Staphylococcus aureus* | 1.8E6 | <200 | <200 | <200 |
| *Enterococcus faecalis* | 1.2E6 | <200 | <200 | <200 |
| *Candida albicans* | 1.2E6 | <200 | <200 | <200 |
| *Aspergillus niger* | 1.7E6 | <200 | <200 | <200 |

Example 2

Inventive Example

| Microorganisms | Inoculum CFU/g | (T2M/45) CFU/g | | |
|---|---|---|---|---|
| | | 7 Days | 14 Days | 28 Days |
| *Escherichia coli* | 1.9E6 | <200 | <200 | <200 |
| *Pseudomonas aeruginosa* | 2.1E6 | <200 | <200 | <200 |
| *Staphylococcus aureus* | 1.4E6 | <200 | <200 | <200 |
| *Enterococcus faecalis* | 1.2E6 | <200 | <200 | <200 |
| *Candida albicans* | 2.1E6 | <200 | <200 | <200 |
| *Aspergillus niger* | 1.5E6 | <200 | <200 | <200 |

Example 3

Inventive Example

| Microorganisms | Inoculum CFU/g | (T2M/45) CFU/g | | |
|---|---|---|---|---|
| | | 7 Days | 14 Days | 28 Days |
| *Escherichia coli* | 1.5E6 | <200 | <200 | <200 |
| *Pseudomonas aeruginosa* | 2.0E6 | <200 | <200 | <200 |
| *Staphylococcus aureus* | 1.2E6 | <200 | <200 | <200 |

-continued

| Microorganisms | Inoculum CFU/g | (T2M/45) CFU/g | | |
|---|---|---|---|---|
| | | 7 Days | 14 Days | 28 Days |
| Enterococcus faecalis | 1.4E6 | <200 | <200 | <200 |
| Candida albicans | 2.4E6 | <200 | <200 | <200 |
| Aspergillus niger | 1.5E6 | <200 | <200 | <200 |

In the inventive examples 1-3, the test products have passed the initial preservative challenge test, and were further subjected to the accelerated aging process by storing the test products in the 45° C. for a period of 8 weeks, as indicated in the tables as T2M data, prior to additional preservative challenge test. For Examples 1-3, all test products have met the preservative criteria for T0M and T2M, and are therefore suitable to be packed in all packaging types, including pots and jars.

Example 4

Comparative Example

| Microorganisms | Inoculum CFU/g | (T0M/25) CFU/g 7 Days |
|---|---|---|
| Escherichia coli | 2.0E6 | <200 |
| Enterococcus faecalis | 1.9E6 | 6.1E5 |
| Candida albicans | 2.7E6 | <200 |
| Aspergillus niger | 2.4E6 | <200 |

In comparative example 4, an inadequate preservative system was present, even with the addition of ethanol. As a consequence, the test product failed T0M preservative challenge test and thus is not deemed suitable for consumer use.

Example 5

Comparative Example

| Microorganisms | Inoculum CFU/g | (T0M/25) CFU/g 7 Days |
|---|---|---|
| Escherichia coli | 1.9E6 | 5.4E5 |
| Enterococcus faecalis | 2.5E6 | 2.0E6 |
| Candida albicans | 1.2E6 | <200 |
| Aspergillus niger | 2.0E6 | 1.7E6 |

In comparative example 5, an inadequate preservative system was present. As a consequence, the test product failed T0M preservative challenge test and is thus not suitable for consumer use.

Example 6

Comparative Example

| Microorganisms | Inoculum CFU/g | (T0M/25) CFU/g 7 Days |
|---|---|---|
| Escherichia coli | 1.9E6 | <200 |
| Enterococcus faecalis | 2.5E6 | <200 |
| Candida albicans | 1.2E6 | <200 |
| Aspergillus niger | 2.0E6 | <200 |

In comparative example 6, caprylyl glycol was added as part of the preservative system. The test product passed the initial preservative challenge test (T0M). However, the test product was found to be unstable due to phase separation which was noted a few weeks after the formula was made. Therefore, accelerated (T2M) challenge test was not performed.

Example 7

Comparative Example

| Microorganisms | Inoculum CFU/g | (T0M/25) CFU/g 7 Days |
|---|---|---|
| Escherichia coli | 2.0E6 | <200 |
| Enterococcus faecalis | 1.7E6 | 1.4E6 |
| Candida albicans | 2.1E6 | <200 |
| Aspergillus niger | 1.9E6 | <200 |

In comparative example 7, an inadequate preservative system was present. As a consequence, the test product failed T0M preservative challenge test and is thus not suitable for consumer uses.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:
1. A composition comprising:
  (a) an aqueous phase having a preservative system containing:
    (i) from about 0.01% to about 1% by weight of at least one aromatic alcohol;
    (ii) from about 0.01% to about 1% by weight of at least one aromatic carboxylic acid chosen from para-anisic acid, anisic acid, caffeic acid, chlorogenic acid, diphenolic acid, ferulic acid, hippuric acid, hydroxycinnamic acid, phenylthioglycolic acid, salicylic acid, acetylsalicylic acid, phthalic acid, salified forms thereof, and combinations thereof; and

(iii) from about 0.01% to about 0.5% by weight of at least one chlorophenyl glyceryl ether, all weights based on the total weight of the composition; and (b) an oil phase comprising (i) at least one emulsifying crosslinked siloxane elastomer selected from the group consisting of substituted dimethicone/copolyol crosspolymer, unsubstituted dimethicone/copolyol crosspolymer, dimethicone and dimethicone/PEG- 10/15 crosspolymers, substituted dimethicone/polyglyceryl crosspolymer, unsubstituted dimethicone/polyglyceryl crosspolymer, and dimethicone and dimethicone/polyglycerin-3 crosspolymer;

wherein the composition is a water-in-oil emulsion and the preservative system includes an effective amount of each of the at least one aromatic alcohol, the at least one aromatic carboxylic acid and the at least one chlorophenyl glyceryl ether, together, to inhibit microorganism proliferation in the composition independent from any activity of parabens, ethanol and/or glycols having $C_5$ to $C_{12}$ alkyl chains, as preservatives; and wherein the composition does not contain any glycol or paraben.

2. The composition of claim 1, wherein the composition is ethanol-free.

3. The composition of claim 1, wherein (a)(i) is chosen from benzyl alcohol, benzoylisopropanol, phenoxyethanol, dichlorobenzyl alcohol, methylphenylbutanol, phenoxyisopropanol, phenylisohexanol, phenylpropanol, phenylethyl alcohol, and combinations thereof.

4. The composition of claim 3, wherein (a)(i) is phenoxyethanol.

5. The composition of claim 1, wherein (a)(i) is present in an amount of from about 0. 1% to about 0.8% by weight, based on the total weight of the composition.

6. The composition of claim 1, wherein (a)(ii) is p-anisic acid.

7. The composition of claim 1, wherein (a)(ii) is present in an amount of from about 0.05% to about 0.5% by weight, based on the total weight of the composition.

8. The composition of claim 1, wherein (a)(iii) is chlorphenesin.

9. The composition of claim 1, wherein (a)(iii) is present in an amount of from about 0.05% to about 0.4% by weight, based on the total weight of the composition.

10. The composition of claim 1 wherein the aqueous phase has a pH ranging from about 4 to about 6.7.

11. The composition of claim 1 wherein (b)(i) of the oil phase comprises the at least one emulsifying crosslinked siloxane elastomer present from about 0.1% to about 20% by weight, based on the weight of the composition.

12. A composition comprising:

(a) an aqueous phase having a preservative system containing:

(i) from about 0.2% to about 0.7% by weight of phenoxyethanol;

(ii) from about 0.1% to about 0.3% by weight of p-anisic acid; and (iii) from about 0.1% to about 0.3% by weight of chlorphenesin, all weights based on the total weight of the composition; and (b) an oil phase comprising (i) at least one emulsifying crosslinked siloxane elastomer selected from the group consisting of substituted dimethicone/copolyol crosspolymer, unsubstituted dimethicone/copolyol crosspolymer, dimethicone and dimethicone/PEG-10/15 crosspolymers, substituted dimethicone/polyglyceryl crosspolymer, unsubstituted dimethicone/polyglyceryl crosspolymer, and dimethicone and dimethicone/polyglycerin-3 crosspolymer;

wherein the composition is a water-in-oil emulsion and the preservative system includes an effective amount of each of the at least one aromatic alcohol, the at least one aromatic carboxylic acid and the at least one chlorophenyl glyceryl ether, together, to inhibit microorganism proliferation in the composition, and the composition is ethanol-free and wherein the composition does not contain any glycols or paraben.

13. The composition of claim 12, wherein (b)(i) of the oil phase comprises the at least one emulsifying crosslinked siloxane elastomer present from about 0.1% to about 20% by weight, based on the weight of the composition.

14. The composition of claim 12, wherein the aqueous phase has a pH ranging from about 4 to about 6.7.

15. The composition of claim 1, wherein the aqueous phase further comprises propanediol.

16. The composition of claim 12, wherein the aqueous phase further comprises propanediol.

17. A composition comprising:

(a) an aqueous phase having a preservative system containing:

(i) from about 0.2% to about 0.7% by weight of phenoxyethanol;

(ii) from about 0.1% to about 0.3% by weight of p-anisic acid; and (iii) from about 0.1% to about 0.3% by weight of chlorphenesin, all weights based on the total weight of the composition; and (b) an oil phase comprising (i) at least one emulsifying crosslinked siloxane elastomer selected from the group consisting of substituted dimethicone/copolyol crosspolymer, unsubstituted dimethicone/copolyol crosspolymer, dimethicone and dimethicone/PEG-10/15 crosspolymers, substituted dimethicone/polyglyceryl crosspolymer, unsubstituted dimethicone/polyglyceryl crosspolymer, and dimethicone and dimethicone/polyglycerin-3 crosspolymer; and (ii) one or more of silicone oils, present from about at least 5 percent up to 45 percent by weight, based upon the weight of the composition; and hydrocarbon-comprising oil(s), present up to 40 percent by weight, based upon the weight of the composition; and and combinations of these;

(c) one or more of (i) aesthetic modifiers selected from the group consisting of Nylon-12, polymethyl silsesquioxane, styrene/acrylates copolymer, silica, starches, modified starches, and silicone resins; and (ii) adjuvants selected from the group consisting of fatty substances, organic solvents, ionic thickeners, nonionic thickeners, hydrophilic thickeners, lipophilic thickeners, softeners, humectants, opacifiers, stabilizers, emollients, silicones, antifoams, fragrances, anionic surfactants, cationic surfactants, nonionic surfactants, zwitterionic surfactants, and amphoteric surfactants, skin care active agents, fillers, propellants, acidifying agents, basifying agents, co-emulsifiers;
(iii) and combinations of these
wherein the composition is a water-in-oil emulsion and the preservative system includes an effective amount of each of the at least one aromatic alcohol, the at least one aromatic carboxylic acid and the at least one chlorophenyl glyceryl ether, together, to inhibit microorganism proliferation in the composition, and the composition is ethanol-free and does not contain any glycol or paraben.

18. The composition of claim 1, further comprising in the oil phase one or more of
silicone oils, present from about at least 5 percent up to 45 percent by weight, based upon the weight of the composition, and
hydrocarbon-comprising oil(s), present up to 40percent by weight, based upon the weight of the composition; and combinations of these.

19. The composition of claim 1, further comprising one or more of
aesthetic modifiers selected from the group consisting of Nylon-12, polymethylsilsesquioxane, styrene/acrylates copolymer, silica, starches, modified starches, and silicone resins; and
adjuvants selected from the group consisting of fatty substances, organic solvents, ionic thickeners, nonionic thickeners, hydrophilic thickeners, lipophilic thickeners, softeners, humectants, opacifiers, stabilizers, emollients, silicones, antifoams, fragrances, anionic surfactants, cationic surfactants, nonionic surfactants, zwitterionic surfactants, and amphoteric surfactants, skin care active agents, fillers, propellants, acidifying agents, basifying agents, co-emulsifiers;
and combinations of these.

* * * * *